United States Patent [19]

Goodale et al.

[11] 4,243,049

[45] Jan. 6, 1981

[54] METHOD AND APPARATUS FOR EXFOLIATIVE CYTOLOGY

[76] Inventors: Robert L. Goodale, 1903 Kenwood Pkwy., Minneapolis, Minn. 55405; Thomas D. Dressel, 1409 Zealad Ave. North, Minneapolis, Minn. 55427; John W. Borner, 9960 Linnet St. NW., Coon Rapids, Minn. 55433

[21] Appl. No.: 47,222

[22] Filed: Jun. 11, 1979

[51] Int. Cl.³ .............................................. A61B 10/00
[52] U.S. Cl. .................................... 128/757; 128/758; 128/304
[58] Field of Search ............... 128/751, 752, 757, 758, 128/304, 305, 311, 749

[56] References Cited

U.S. PATENT DOCUMENTS

| | | | |
|---|---|---|---|
| 2,955,592 | 10/1960 | MacLean | 128/757 |
| 3,230,949 | 1/1966 | Olleros | 128/752 |

*Primary Examiner*—Kyle L. Howell
*Attorney, Agent, or Firm*—John W. Adams

[57] ABSTRACT

A method of obtaining actual tumor cells from remote, previously inaccessible anatomical locations and apparatus for carrying out said method, which includes a miniature cell-scraping rasp of an extremely small size which was previously unavailable and which is particularly adapted to be passed into the far reaches of inaccessible anatomic organs. The method and the rasp are particularly adaptable to abrade the epithelium of ductal areas and produce exfoliation of cells and facilitate collections of the cells for cytologic diagnosis.

8 Claims, 4 Drawing Figures

METHOD AND APPARATUS FOR EXFOLIATIVE CYTOLOGY

BACKGROUND OF THE INVENTION

This invention relates to the general field of exfoliative cytology, which includes such well-known procedures as the cervical "pap test," gastric, esophageal, and bronchial brush cytology, and peritoneal and pleural fluid cytology. The field also includes renal, ureteral cytology, hepaticobiliary cytology.

These procedures have previously been limited by the fact that the cell-collecting methods and instruments have been too large (a minimum of 1 mm in diameter). This limitation has prevented early diagnosis of the presence of malignant cells in remote ductal areas such as the pancreatic duct, where a very substantial number of malignancies occur.

DESCRIPTION OF THE PRIOR ART

The inventors of this invention hereby state and represent that the following prior art is the closest known to them at this time of filing of this application:

Plastic bristle brushes have previously provided the smallest-size cell-abrading instruments available to the medical profession for exfoliative cytologic diagnosis. The smallest-size plastic bristle brushes that are available to the profession are 1.0 mm in diameter, which is too large for insertion into the pancreatic duct and other anatomic duct areas. Efforts to have small-diameter brushes produced have been unsuccessful. For this reason it has previously been impossible to obtain cells from such areas as the epithelium of the pancreatic duct area, and this has required the use of the duodenal fluid aspiration method, which produces a relatively low yield of specimen cells for diagnosis. This problem is further accentuated by the fact that the yield from such an aspiration procedure is substantially lower in the remote reaches of the pancreas than at the head end thereof.

SUMMARY OF THE INVENTION

The apparatus disclosed herein embodies a rasp approximately 1.0 mm long and 0.35 mm in diameter, which includes a plurality of axially spaced apart grooves which form spaced circumferential ridges or rings. The grooves are cut in such a way that the outer edges of the ridges are relatively sharp and form scraping edges which abrade the epithelium surfaces and cause exfoliation of the cells. The orientation and depth of the grooves are designed to produce a configuration of the ridges so that the maximum abrading or shearing force applied to the ductal cells is produced as the device is advanced into the duct, and minimal shearing or abrasive forces are produced as the device is withdrawn. The grooved areas provide collection areas within which some abraded cells which have been exfoliated are collected and removed from the duct. Additional exfoliated cells are also removed by fluid aspiration. This permits a very high yield of collected cells and therefore greatly facilitates the diagnostic procedures, and in addition to the collection of cells for diagnosis, the rasp element could prove to be important as a therapeutic instrument for removal of cells to clean the epithelium of small, remote ductal structures.

The invention also includes the method of exfoliating cells from remote ductal areas by abrading the surfaces thereof with a rasp of a size smaller than 1.0 mm in diameter. The small size and extreme flexibility of the device permit highly efficient abrasion of the ductal structures to obtain, for exfoliative cytologic examination, maximum collection of cells from previously inaccessible anatomic organs.

DETAILED DESCRIPTION OF A PREFERRED EMBODIMENT OF THE INVENTION

Figure 1:
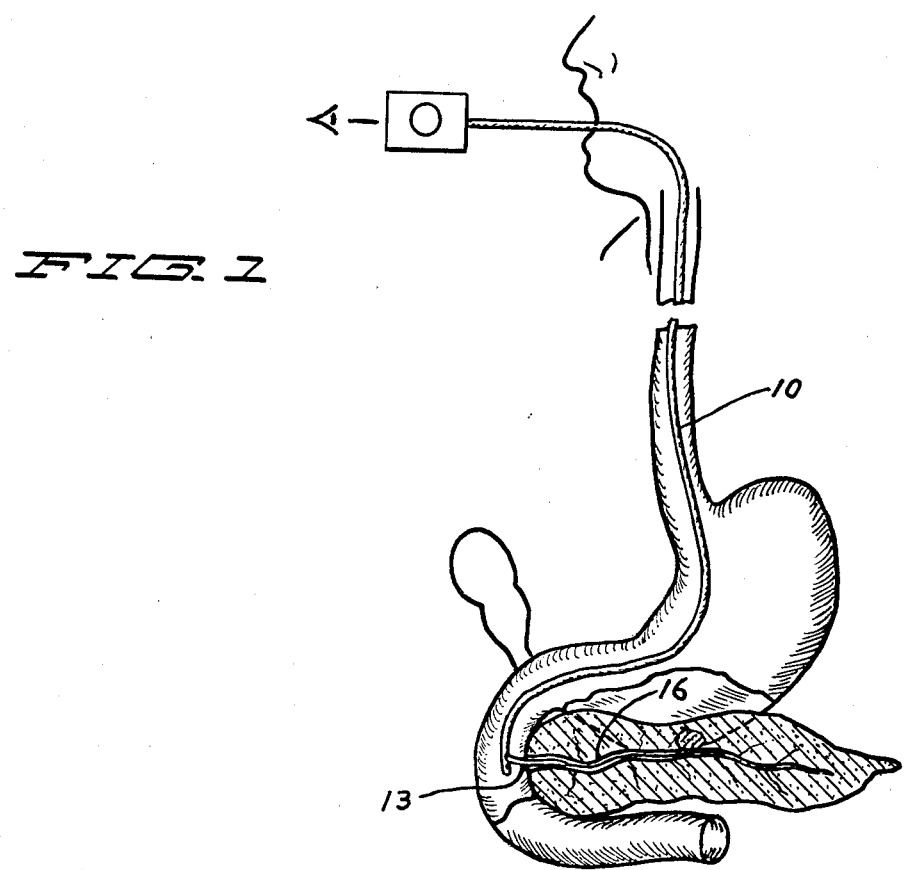
FIG. 1 is a diagrammatic sectional view of the esophagus, stomach and pancreas showing an endoscope with a rasp embodying the invention inserted through the endoscope and shown in operative position within the pancreatic duct.

FIG. 1 shows the lower end of a conventional endoscope 10 which has been inserted through the patient's mouth, esophagus, and stomach into the duodenum area adjacent to the entrance 12a to the pancreatic duct 12. A catheter 13, having a diameter of approximately 1 mm and having a beveled leading end 13a, is inserted through the endoscope 10 and entrance 12a and provides a guiding tube through the entrance of ampulla 12a and into the pancreatic duct 12. A tumor 12b is shown in the pancreas and has exposed portions along the pancreatic duct.

A suitable operating wire (not shown) is inserted down through the endoscope 10 within the catheter 13 and has a small diameter lead wire 16 attached to the lower end thereof. The serrated cell-scraping rasp 20 is formed on the free end of the lead wire 16. The diameter of the lead wire 16 is less than 1.0 mm and, in the form shown, is approximately 0.35 mm, and the length thereof is approximately 15 cm. This is a highly flexible wire and in the preferred embodiment is constructed from a three-stranded stainless steel material, although there are other constructions and materials which are suitable for this purpose and the specific material and construction of the lead wire are not critical limitations of the invention.

Figure 2:
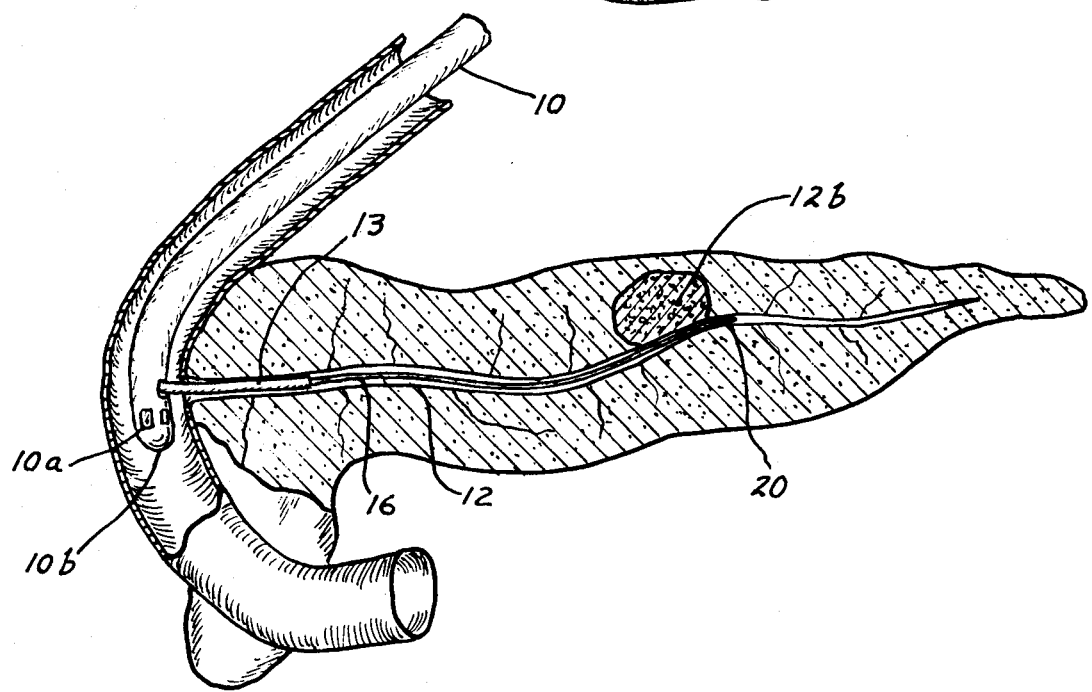
FIG. 2 is a slightly enclosed sectional view showing the entire pancreatic duct with the rasp positioned therein.
Figure 3:
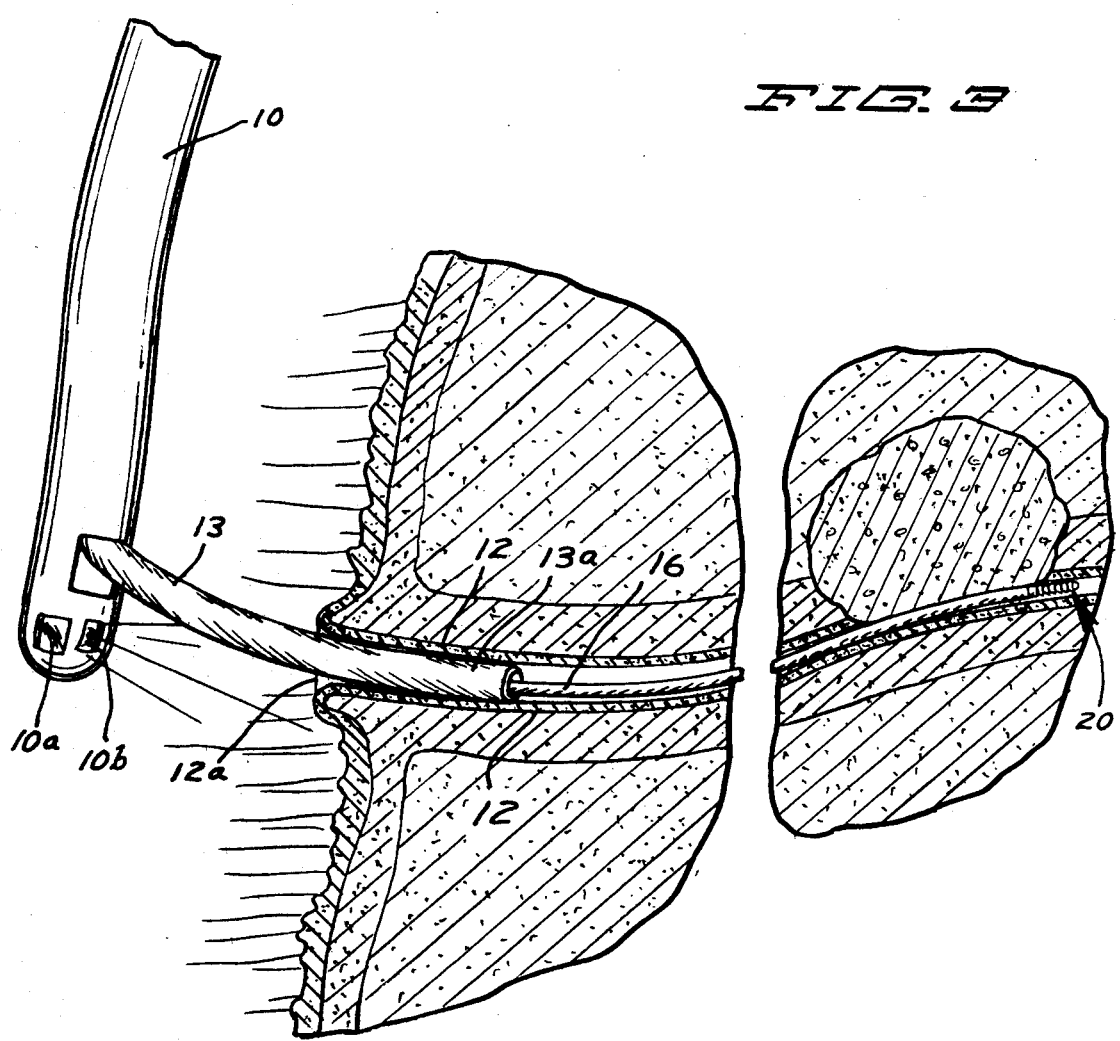
FIG. 3 is greatly enlarged sectional view of portions of the pancreatic duct and the rasp positioned therein; and, FIG. 4 is an enlaged elevational view showing the rasp, per se, with exfoliated.
Figure 4:
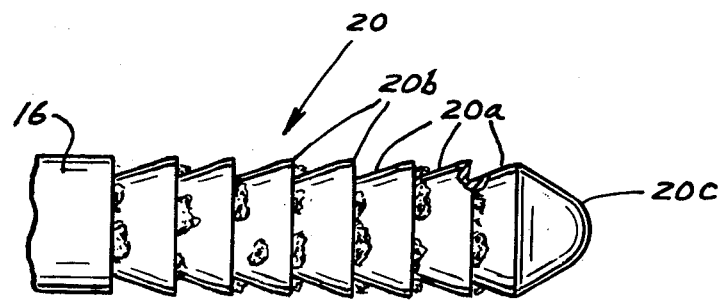

The rasp 20 is formed on the free end of the lead wire 16 and may be conveniently constructed by applying silver solder to the tip of the three-strand wire for approximately 1 mm in length and thereafter cutting circumferential grooves 20a around the silver-solder portion, which is also approximately 0.35 mm in diameter. The grooves are axially spaced apart a sufficient distance to permit the cutting edges of the cutting ridges 20b to produce efficient abrading and shearing forces on the engaged ductal cells. The grooves are tapered to produce maximum abrasion action as the rasp is advanced, with minimal or no abrasion or shearing action as the rasp is withdrawn. The tip 20c of the rasp is rounded, as shown in FIG. 2. The trailing ends of each of the grooves 20a are clightly undercut, as shown in fragmentary section in FIG. 2, to produce a relatively sharp scraping edge around the periphery of each ridge 20b.

The diameter of the entrance portion of the pancreatic duct is approximately 1 mm and the duct gradually diminishes inwardly in diameter as shown. For clarity in the drawings, the pancreatic duct is shown somewhat larger relative to the size of of the rasp 20 and lead wire 16 than is actually true in practice. While it is possible to insert the smooth surfaced catheter 13 having the beveled lead end 13a through the sphincter 12a of the duct, it is not possible to insert a rough surfaced brush element 1 mm diameter into the duct and prior to the conception of the present small diameter rasp element, it has been impossible to obtain any abrading action within such small duct areas as the pancreatic duct.

METHOD OF OBTAINING SAMPLE CELLS

The endoscope 10 is initially inserted through the patient's mouth, down through the esophagus and stomach, to the area of the duodenum. The lower end of the endoscope 10 is conventionally provided with a viewing mirror or prism 10a which is aligned with the lower end of a fiber optic viewing element (not shown) having its upper end located at the upper end of the endoscope. A light 10b is also conveniently provided at the lower end of the endoscope in order to assist in locating the entrance 12a to the pancreatic duct 12. When the endoscope has been properly positioned adjacent to the pancreatic duct entrance 12a, the catheter 13 is inserted down through the endoscope 10 and into the duct 12, as illustrated. After the catheter has been properly inserted through the sphincter at the duct entrance 12a, the cable 16 with the rasp 20 attached at the free end thereof, is inserted down through the catheter and into the pancreatic duct 12. As the rasp travels into the duct, it will scrape the epithelium and remove sample cells therefrom. If there is a tumor such as the tumor 12b, samples from the tumor can be collected. The dislodged cells that are not collected in the grooves of the rasp 20 may be aspirated from the duct 12 through the catheter 13, thus increasing the ultimate yield of cells produced from the scraping process.

It will be seen that this invention provides a method and apparatus for producing, by a scraping action, exfoliation of cells directly from critical epithelium areas such as the pancreatic duct, which have been previously inaccessible to direct exfoliation of such cells.

What is claimed is:

1. The method for exfoliative abrasion of cells from the inner portions of the pancreatic duct and other inaccessible anatomical locations;
   said method including the following steps;
   providing a serrated rasp element of a diameter less than 1.0 mm,
   inserting an endoscope down through the patient's mouth, esophagus, and stomach to locate the lower end thereof in substantially opposed relation to the entrance to the pancreatic duct,
   providing flexible operating means for said rasp element,
   inserting said operating means and rasp element downwardly through said endoscope and through the entrance of said pancreatic duct,
   engaging the epithelium of the desired ductal areas by a scraping action of the serrated rasp element to abrade the same and produce exfoliation of cells therefrom,
   collecting said exfoliated cells, and
   withdrawing said rasp and endoscope back through the patient's mouth.

2. The method set forth in claim 1 and providing a guiding catheter tube,
   extending said tube downwardly through said endoscope and through the entrance of said pancreatic duct, and
   inserting said operating means and said rasp through said catheter into the pancreatic duct.

3. Apparatus for abrading cells from the inner portions of the pancreatic duct and similar inaccessible anatomical locations,
   a serrated rasp element of a size less than 1.0 mm in diameter,
   flexible operating means attached at one end of said rasp, and
   means for guiding said rasp and said operating means down through the mouth, esophagus and stomach of the patient and through the entrance of the pancreatic duct into inner portions of said duct where sample cells are to be abraded and collected.

4. The structure set forth in claim 3 wherein the serrations of said rasp are formed by grooved portions producing cutting ridge portions.

5. The structure set forth in claim 3 wherein the serrations of said rasp are formed by a plurality of axially spaced circumferential grooves producing circumferential cutting ridges.

6. The structure set forth in claim 5 wherein the leading portions of the surfaces formed by said grooves are generally frusto-conical decreasing in diameter toward the trailing ends thereof, to form the cutting ridge at the trailing ends of the respective grooves, whereby the scraping and cell-collecting action of the rasp occurs during the forward movement of the rasp into the duct.

7. The structure set forth in claim 5 wherein the trailing ends of said grooves are undercut to produce an effective peripheral cutting edge and collection area adjacent thereto.

8. The structure set forth in claim 3 wherein the forward end of said rasp has a rounded, tapered nose to guide said rasp through the duct.

* * * * *

UNITED STATES PATENT AND TRADEMARK OFFICE
CERTIFICATE OF CORRECTION

PATENT NO. : 4,243,049

DATED : January 6, 1981

INVENTOR(S) : Robert L. Goodale et al

It is certified that error appears in the above—identified patent and that said Letters Patent is hereby corrected as shown below:

In Column 1, following line 5 under the title Insert

-- The invention described herein was made in the course of work under a grant or an award from the Department of Health and Human Service. --.

Signed and Sealed this

Eighth Day of September 1981

[SEAL]

*Attest:*

*Attesting Officer*

GERALD J. MOSSINGHOFF

*Commissioner of Patents and Trademarks*